(12) United States Patent
Boyers et al.

(10) Patent No.: US 12,702,405 B2
(45) Date of Patent: Aug. 11, 2026

(54) ASYMMETRIC CLIP APPLIER AND CARTRIDGE

(71) Applicant: TELEFLEX MEDICAL LLC, Morrisville, NC (US)

(72) Inventors: Jessica Boyers, Morrisville, NC (US); Alexandria De Jong, Fuquay Varina, NC (US)

(73) Assignee: TELEFLEX MEDICAL LLC, Morrisville, NC (US)

( * ) Notice: Subject to any disclaimer, the term of this patent is extended or adjusted under 35 U.S.C. 154(b) by 371 days.

(21) Appl. No.: 17/964,834

(22) Filed: Oct. 12, 2022

(65) Prior Publication Data

US 2023/0124563 A1 Apr. 20, 2023

Related U.S. Application Data

(60) Provisional application No. 63/255,926, filed on Oct. 14, 2021.

(51) Int. Cl.
*A61B 17/04* (2006.01)

(52) U.S. Cl.
CPC .. *A61B 17/0487* (2013.01); *A61B 2017/0488* (2013.01)

(58) Field of Classification Search
CPC . A61B 17/0487; A61B 17/128; A61B 17/122; A61B 17/04; A61B 17/1285; A61B 17/1222; A61B 2017/0488; A61B 17/1227; A61B 17/105; A61B 17/083; A61B 17/068; A61B 17/076; A61B 17/10; A61B 17/28; A61B 17/29; A61B 2017/2936; A61B 2017/2933; A61B 2017/2825; A61B 2017/00831; A61B 2017/00862; A61B 2017/00884; A61B 2017/0053;
(Continued)

(56) References Cited

U.S. PATENT DOCUMENTS 5,163,945 A 11/1992 Ortiz et al.
6,391,035 B1 * 5/2002 Appleby .............. A61B 17/128 606/142
(Continued)

FOREIGN PATENT DOCUMENTS

JP 2006-175225 A 7/2006
JP 2020-511263 A 4/2020
(Continued)

*Primary Examiner* — Shaun L David
*Assistant Examiner* — Cherie M Poland
(74) *Attorney, Agent, or Firm* — Baker Hostetler

(57) ABSTRACT

A clip applier may include: a first jaw member for engaging a first leg member of a surgical clip; and a second jaw member for engaging a second leg member of the surgical clip. At least one of the first jaw member and the second jaw member is asymmetric about a medial plane of the clip applier. A clip cartridge may include: a base having a first axis and a second axis, the second axis being perpendicular to the first axis; and a plurality of walls defining at least one cavity for receiving the surgical clip. At least one of the plurality of walls has a first wall portion on a first side of the first axis and a second wall portion on a second side of the first axis. The first wall portion and the second wall portion are offset to each other with respect to the second axis.

12 Claims, 6 Drawing Sheets

(58) Field of Classification Search
CPC ........... A61B 2017/00473; A61B 2017/00367; A61B 2017/00296; A61B 2017/0048
See application file for complete search history.

(56) References Cited

U.S. PATENT DOCUMENTS

| | | | | |
|---|---|---|---|---|
| 6,419,682 | B1 * | 7/2002 | Appleby ............ | A61B 17/1222 206/339 |
| 6,733,514 | B2 | 5/2004 | Miser | |
| 10,932,792 | B2 | 3/2021 | Stokes et al. | |
| 2003/0014060 | A1 | 1/2003 | Don et al. | |
| 2004/0040875 | A1 * | 3/2004 | Gallagher .......... | A61B 17/1222 206/399 |
| 2004/0097971 | A1 * | 5/2004 | Hughett ............. | A61B 17/1285 606/142 |
| 2006/0124485 | A1 | 6/2006 | Kennedy | |
| 2010/0274263 | A1 * | 10/2010 | Disch ................. | A61B 17/1285 606/142 |
| 2018/0271527 | A1 * | 9/2018 | Shellenberger .... | A61B 17/1285 |
| 2018/0271534 | A1 * | 9/2018 | Shellenberger .... | A61B 17/1222 |
| 2018/0271535 | A1 | 9/2018 | Shellenberger et al. | |
| 2019/0046197 | A1 | 2/2019 | Stokes et al. | |
| 2019/0357913 | A1 * | 11/2019 | Pilletere ............. | A61B 17/1285 |
| 2021/0007751 | A1 * | 1/2021 | Shellenberger .... | A61B 17/1285 |
| 2021/0128159 | A1 * | 5/2021 | Taylor ................ | A61B 17/1222 |

FOREIGN PATENT DOCUMENTS

| | | | | |
|---|---|---|---|---|
| JP | 2020-529895 | A | 10/2020 | |
| WO | 2020018784 | | 1/2020 | |
| WO | WO-2020018784 | A1 * | 1/2020 | ......... A61B 17/1285 |
| WO | 2021/062170 | A1 | 4/2021 | |

* cited by examiner 106
128
108
139
W1
MP
W2
W4
W3
122
129
200
140
138
132

14
102
16
133
104
140
128
123
126
122
124
129
136
132
134
139
140
138

ASYMMETRIC CLIP APPLIER AND CARTRIDGE

CROSS REFERENCE TO RELATED APPLICATIONS

This application claims the benefit of U.S. Provisional Patent Application No. 63/255,926, filed Oct. 14, 2021, the disclosure of which is incorporated herein by reference in its entirety.

TECHNICAL FIELD

The present disclosure relates generally to medical devices, and more particularly to clips appliers and cartridges for applying a surgical clip to tissue.

BACKGROUND

The ligation of tissue (e.g., blood vessels, lymph nodes, nerves, cystic ducts, or cardiac tissue) is a common practice in many surgical procedures. Current ligation systems often include a surgical clip, a clip applier, and/or a cartridge. The clip applier is used by a user to grasp the surgical clip from the cartridge and to apply the surgical clip to tissue, for example, to ligate a blood vessel (e.g., a vein or an artery).

OVERVIEW

The present inventors recognize that there is a need to improve one or more features of the clip applier systems. For example, current clip appliers are symmetric about a medial plane. This can cause improper loading of the surgical clip due to a poor interface between the clip applier of the cartridge. For example, the cartridge may provide a loose fit of the clip applier, such that clip retention features on the clip applier may not properly align with and engage interfaces on the surgical clip. This may result in the surgical clip being insufficiently secured to the clip applier, which may cause the surgical clip to fall out of the clip applier and/or not be properly applied to tissue.

The disclosed clip appliers, cartridges, and/or clip applier systems are directed to mitigating and/or overcoming one or more of these problems, and/or other problems of the prior art.

A first aspect of the present invention is directed to a clip applier configured to apply a surgical clip, the clip applier including: a first jaw member configured to engage a first leg member of the surgical clip, and a second jaw member configured to engage a second leg member of the surgical clip, wherein at least one of the first jaw member and the second jaw member is asymmetric about a medial plane of the clip applier.

In some embodiments, both of the first jaw member and the second jaw member are asymmetric about the medial plane of the clip applier. In some embodiments, at least one of the first and second jaw members has a first width on a first side of the medial plane of the clip applier and a second width on a second side of the medial plane of the clip applier, and the first width is greater than the second width. In some embodiments, at least one of the first and second jaw members has a first longitudinal wall on a first side of a longitudinal channel and a second longitudinal wall on a second side of the longitudinal channel, and a lateral width of the first longitudinal wall is greater than a lateral width of the second longitudinal wall. In some embodiments, the first jaw member includes a first longitudinal channel extending through a distal end of the first jaw member, and/or the second jaw member includes a second longitudinal channel extending through a distal end of the second jaw member. In some embodiments, the first jaw member includes at least one first recess configured to receive at least one boss on the first leg member, the second jaw member includes at least one second recess configured to receive at least one boss on the second leg member, and at least one of the first jaw member and the second jaw member are asymmetric about the medial plane of the clip applier along the at least one first recess and the at least one second recess. In some embodiments, the first jaw member has a closed lateral side of the at least one first recess, and the second jaw member has a closed lateral side of the at least one second recess. In some embodiments, the at least one first recess of the first jaw member has an open lateral side and a closed lateral side, and the at least one second recess of the second jaw member has an open lateral side and a closed lateral side. In some embodiments, each of the first and second jaw members has an angled distal surface. In some embodiments, the first jaw member and the second jaw member, when assembled, are radially symmetric. In some embodiments, at least one of the first and second jaw members includes a stabilizing member configured to laterally stabilize a proximal portion of the surgical clip when the surgical clip is in an open configuration. In some embodiments, the clip applier further includes a longitudinal channel in at least one of the first and second jaw members configured to receive the stabilizing member of the at least one of the first and second jaw members when the clip applier is in a closed configuration. In some embodiments, the first jaw member includes a first stabilizing member, the second jaw member includes a second stabilizing member, and the first stabilizing member and the second stabilizing member are configured to receive the proximal portion of the surgical clip when the surgical clip is in an open configuration. In some embodiments, the first jaw member and the second jaw member are at least substantially identical.

A second aspect is directed to a clip applier system including: the clip applier as discussed above; and a clip cartridge having at least one cavity configured to receive the clip applier to load the surgical clip, wherein the at least one cavity is asymmetric about a medial plane. In some embodiment, the at least one cavity is radially symmetric. In some embodiments, the at least one cavity is formed by offset wall portions of the clip cartridge.

A third aspect of the invention is directed to a clip cartridge configured to store at least one surgical clip, the clip cartridge including: a base having a first axis and a second axis, the second axis being perpendicular to the first axis; and a plurality of walls defining at least one cavity configured to receive the at least one surgical clip, wherein at least one of the plurality of walls has a first wall portion on a first side of the first axis and a second wall portion on a second side of the first axis, and the first wall portion and the second wall portion are offset to each other with respect to the second axis.

In some embodiments, each of the plurality of walls have the first wall portion and the second wall portion that are offset to each other with respect to the second axis. In some embodiments, the at least one of the plurality of walls has a central portion between the first wall portion and the second wall portion. In some embodiments, the first wall portion and the second wall portion have a width less than the central portion. In some embodiments, the second axis extending through the center of the central portion is offset to the second axis extending through the center of at least one of the first wall portion and the second wall portion. In some embodiments, the at least one cavity is asymmetric about a medial plane of the cavity. In some embodiments, the at least one cavity is radially symmetric. In some embodiments, the clip cartridge further includes a retainer disposed over the base and configured to releasably retain the at least one surgical clip in the at least one cavity. In some embodiments, the clip cartridge further includes at least one support member extending between adjacent walls of the plurality of walls. In some embodiments, the first axis is a longitudinal axis of the base, and the second axis is a lateral axis of the base.

A fourth aspect of the present invention is a clip applier system including a clip applier and a clip cartridge, as discussed herein.

BRIEF DESCRIPTION OF THE DRAWINGS

In order that the invention may be readily understood, aspects of this invention are illustrated by way of examples in the accompanying drawings.

The same reference numbers are used in the drawings and the following detailed description to refer to the same or similar parts.

DETAILED DESCRIPTION

The present invention is generally directed to cartridges, clip appliers, and/or clip applier assemblies configured to facilitate loading and/or stability of a surgical clip. In some embodiments, the clip applier and clip cartridge may have matching key way interfaces to ensure proper and consistent loading of the surgical clip. The key way interface may be provided by jaw members of the clip applier being asymmetric about a medial plane at least at a distal portion. The asymmetry may be formed by each of the jaw members having a different geometry and/or material on opposing lateral sides of the medial plane. For example, each jaw member may have opposing sides from the medial plane with different widths, defined at least in part by distal portions of longitudinal walls on opposing side of a longitudinal channel. In some embodiments, the jaw members may be at least substantially identical, such that the jaw members are radially symmetric when assembled. The shape of the jaw members may match with a corresponding shape of at least one cavity in the cartridge for reliable loading of the surgical clip. For example, the cartridge may have cavities that are asymmetric about a medial plane matching the widths of the jaw members and formed by staggered wall portions.

Furthermore, the asymmetric jaw members may provide greater jaw structural integrity while minimizing any negative impact to weight and/or visibility. For example, each of the jaw members may have at least one clip retention feature (e.g., a pair of recesses) that are closed on a first lateral side of the jaw member and open on a second lateral side of the jaw member. The closed lateral side may improve the lateral stability of the surgical clip in the jaw members, and assist with preventing the surgical clip from loosening, becoming misaligned and/or falling out as the surgical clip is manipulated into proper position for application, or even when bumped or jostled. The open lateral side of each of the jaw member may allow for visual confirmation of proper loading of a surgical clip interface (e.g., at least one boss member) into the at least one clip retention feature. Thus, the jaw members would not be negatively impacted in visibility and/or clip separation. The jaw members may even further include a slanted or angled distal surface at the tip which assists with initial trocar entry and navigation of the applier jaws intracorporeally.

Figure 1:
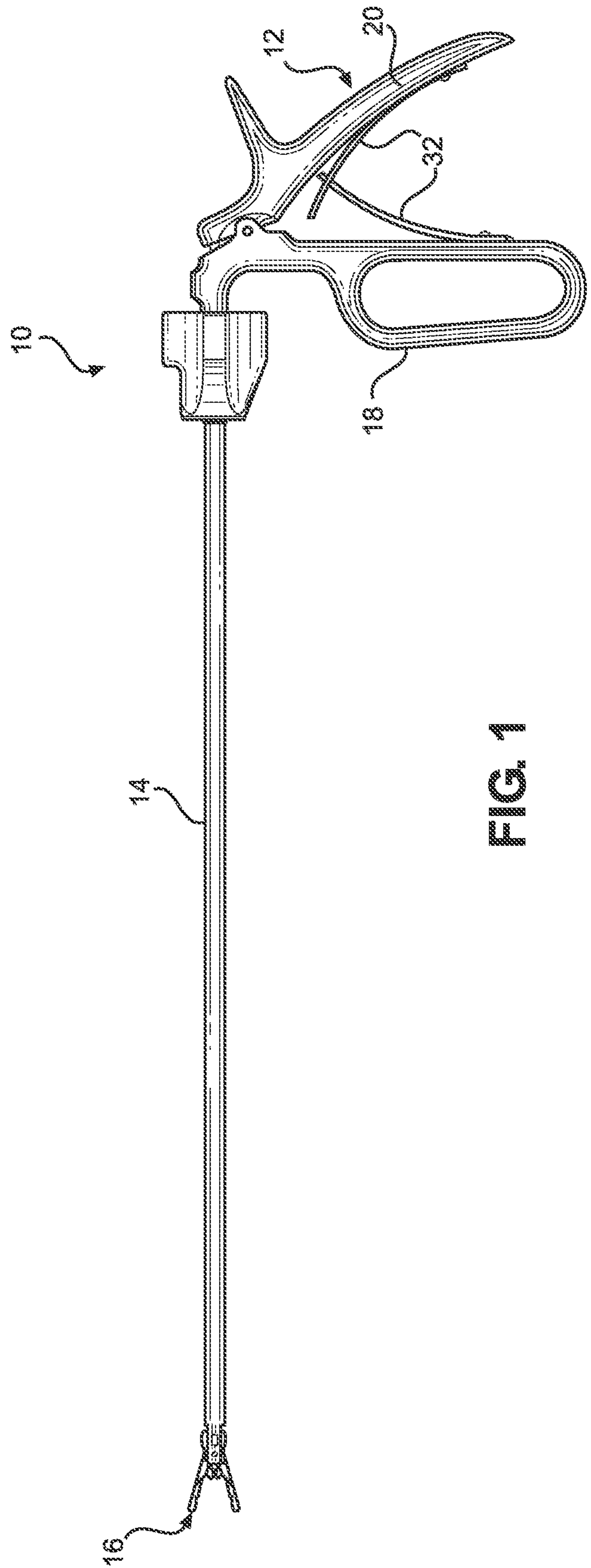
FIG. 1 illustrates a side view of an exemplary embodiment of a clip applier according to the present invention.
Figure 2:
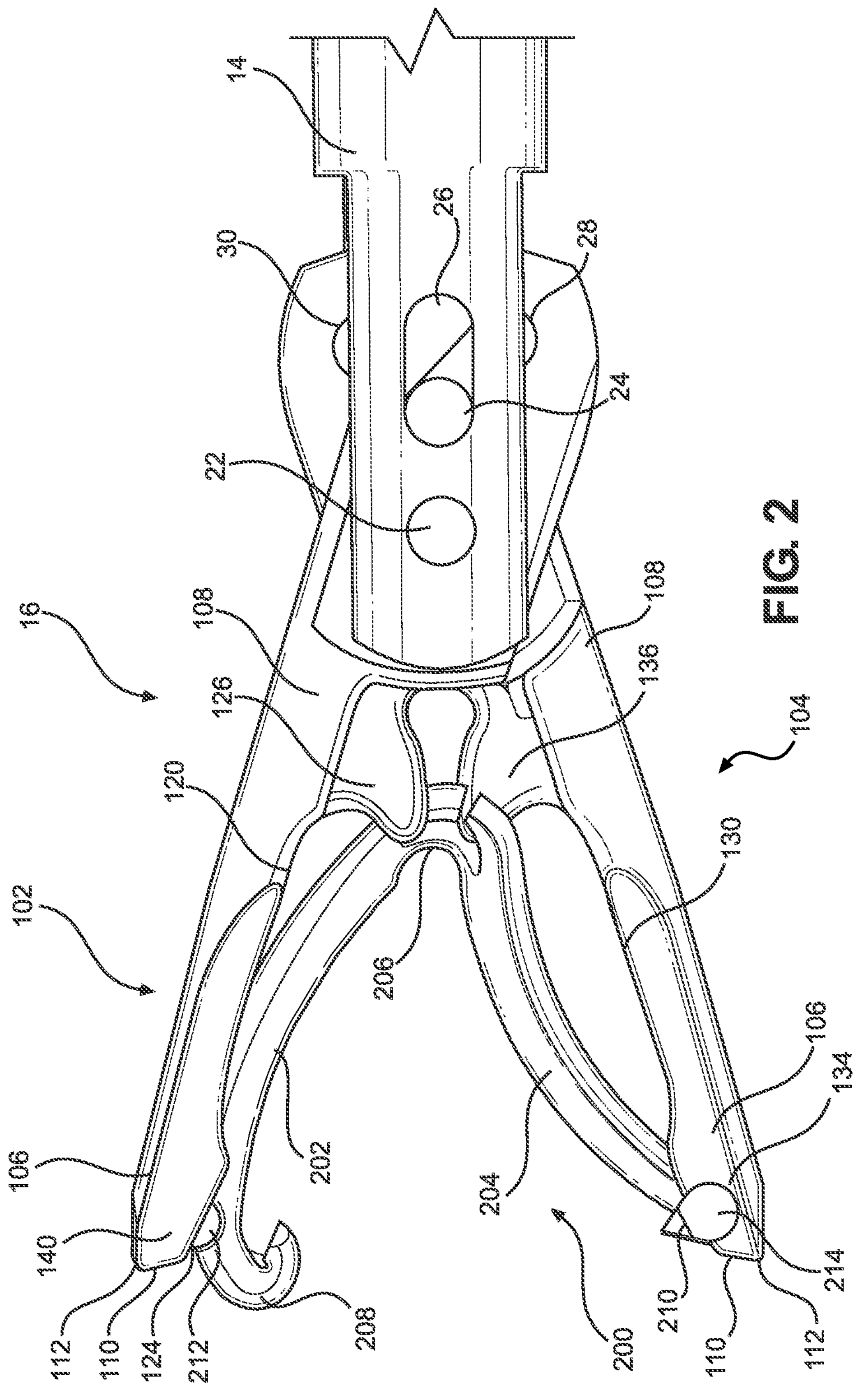
FIG. 2 illustrates aside view of an exemplary embodiment of a jaw mechanism of the clip applier of FIG. 1 loaded with a surgical clip according to the present invention.
Figures 3, 4:
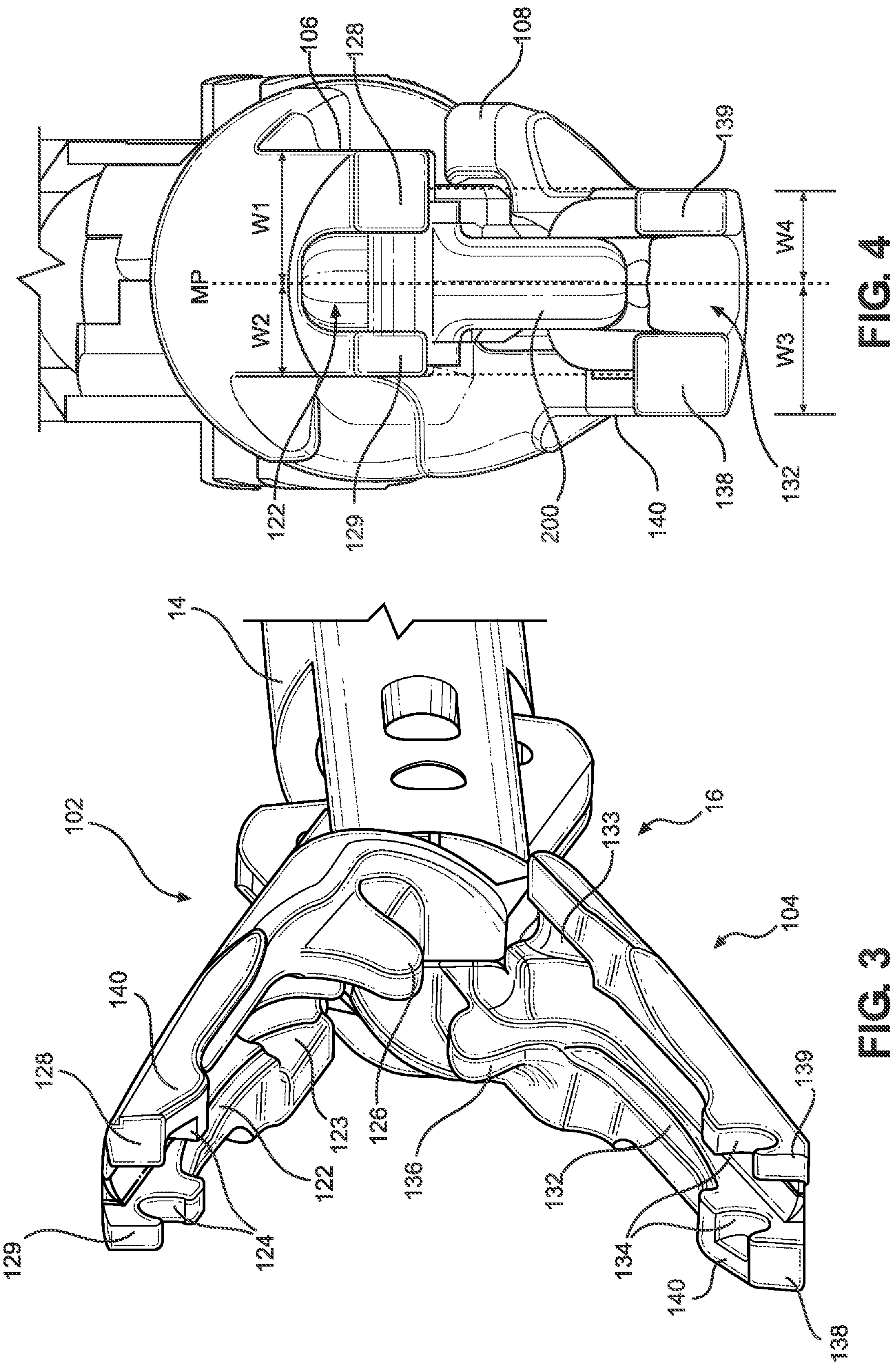
FIG. 3 illustrates a perspective view of the jaw mechanism of the clip applier of FIGS. 1-2.
FIG. 4 illustrates a frontal view of the jaw mechanism of the clip applier of FIGS. 1-3 loaded with the surgical clip.

FIG. 1 illustrates a side view of an exemplary clip applier 10, FIG. 2 illustrates a side view of an exemplary jaw mechanism 16 of the clip applier 10 loaded with a surgical clip 200, and FIG. 3 illustrates a perspective view of the jaw mechanism 16. As illustrated, the clip applier 10 may include a handle mechanism 12 connected to a proximal end of a shaft 14 and the jaw mechanism 16 pivotably connected to a distal end of the shaft 14.

The handle mechanism 12 may include a first handle member 18 and a second handle member 20 movably coupled to each other to actuate the jaw mechanism 16. For example, the first handle member 18 and the second handle member 20 may be pivotably attached. The first handle member 18 may be fixed longitudinally relative to the elongated shaft 14, and the second handle member 20 may be fixed longitudinally relative to an actuator rod (not shown) extending through a lumen of the elongated shaft 14. Pivoting the second handle member 20 relative to the first handle member 18 may longitudinally translate (e.g., retract and/or advance) the actuator rod through the elongated shaft 14 to actuate or pivot the jaw mechanism 16 between an open configuration and a closed configuration about a hinge pin 22. For example, the actuator rod may have one or more drive boss members 24 attached on opposing lateral sides of a distal end. The drive boss members 24 may slide through one or more longitudinal guide channels 26 in the elongated shaft 14 and angled drive channels 28, 30 in each of the first and second jaw members 102, 104. A spring 32 may be disposed between the first handle member 18 and the second handle member 20 to bias the jaw mechanism 16 from the closed or partially closed configuration to the open or partially open configuration. An exemplary handle and actuation mechanism is further discussed in U.S. Pat. No. 6,733,514, the entire disclosure of which is expressly incorporated herein by reference. However, other embodiments of the handle and/or actuation mechanism may be included.

The surgical clip 200 may include a first leg member 202 and a second leg member 204 having proximal end portions pivotably coupled at a hinge member 206. The surgical clip 200 may include one or more latching mechanisms. For example, the first leg member 202 may include a distal end portion having a hook portion 208, and the second leg member 204 may include a distal end portion having a tip member 210. The first leg member 202 and/or the second leg member 204 may be configured to pivot relative to each other between an open configuration and a closed, latched configuration via the hinge member 206. The hook portion 208 may be C-shaped having a convex distal surface and a concave proximal surface. The tip member 210 may include a groove at a distal end. The surgical clip 200 may further include one or more engagement portions. For example, the first leg member 202 may include one or more boss members 212 on the distal end portion proximal of the hook portion 208, and the second leg member 204 may include one or more boss members 214 on the distal end portion at the tip member 210. The one or more boss members 212, 214 may secure the surgical clip 200 to the clip applier 10 during application of the surgical clip 200 to tissue. The one or more boss members 212, 214 may extend laterally from opposing sides of the first and second leg members 202, 204. For example, the first leg member 202 may include boss members 212 extending laterally from opposing sides of the hook portion 208 and connected by a bridge member extending the width of the hook portion 208. The second leg member 204 may include boss members 214 extending laterally from opposing sides of the tip member 210 and separated by the groove in the tip member 210.

The first and second leg members 202, 204 may each have a curvature extending substantially its entire length between the respective proximal and distal end portions. The first leg member may have a convex outer surface and a concave inner surface, and the second leg member 204 may have a concave outer surface and a convex inner surface. The hinge member 206 may have a concave inner surface joining the inner surfaces and a convex outer surface joining the outer surfaces. During closure, the convex outer surface of the hook portion 208 may engage camming beveled surfaces at the tip member 210, and one or both of the leg members 202, 204 may deflect as the leg members 202, 204 are continued to be pressed together. The first leg members 202 may lengthen or straighten and/or the second leg member 204 may compress to accommodate the hook portion 208 deflecting and/or extending around tip member 210. The leg members 202, 204 may revert back to the curvatures in the latched configuration due to the natural resiliency of the surgical clip 200. Thus, the hook portion 208 may receive the tip member 210 in the concave proximal surface in the latched configuration. The radii of curvature of the surfaces of the first leg member 202 and the surfaces of the second leg member 204 may substantially match to provide a relatively even distribution of compressive force applied across the width of the clamped tissue (e.g., a ligated blood vessel). The security of the latching mechanism is ensured when the clamped tissue exerts a counter force against the closure of the surgical clip 200 causing the leg members 202, 204 to deflect and lengthen moving the tip member 210 further into the hook portion 208. Exemplary embodiments of the surgical clip 200 are further disclosed in U.S. Pat. Nos. 4,834,096 and 5,100,416, the entire disclosures of which are expressly incorporated herein by reference. However, other embodiments of the surgical clip may be embodied.

As illustrated in FIGS. 2-4, the jaw mechanism 16 may include a first jaw member 102 configured to engage the first leg member 202 and a second jaw member 104 configured to engage the second leg member 204. The first jaw member 102 and/or the second jaw member 104 may be configured to pivot relative to each other by the hinge pin 22, in order to move the surgical clip 200 between the open and closed configurations. Thus, the jaw mechanism may be configured to be loaded with the surgical clip 20) from a cartridge 300 (e.g., FIGS. 5-7) when in the open configuration and pivot into the closed configuration to apply the surgical clip 200 to tissue.

As further illustrated in FIGS. 2-3, the first jaw member 102 may include a first inner surface 120 having a first longitudinal channel 122, at least one first recess 124 on a distal portion 106 of the first jaw member 102, and a first stabilizing member 126 on a proximal portion 108 of the first jaw member 102. The first longitudinal channel 122 may separate a first longitudinal wall 128 and a second longitudinal wall 129 of the first jaw member 102. The second jaw member 104 may include a second inner surface 130 having a second longitudinal channel 132, at least one second recess 134 on a distal portion 106, and a second stabilizing member 136 on a proximal portion 108. The second longitudinal channel 132 may separate a third longitudinal wall 138 and a fourth longitudinal wall 139 of the second jaw member 104. In some embodiments, at least one of the first and second longitudinal channels 122, 132 may extend through the distal ends of the respective first and second jaw member 102, 104, thus separating the distal ends of the first and second longitudinal walls 128, 129 and/or the distal ends of the third and fourth longitudinal walls 138, 139. However, in some embodiments, at least one of the first and second jaw members 102, 104 may be closed at the distal end, such that the respective longitudinal walls 128, 129, 138, 139 may join to close the respective longitudinal channel 122, 132. Each of the first and second longitudinal walls 128, 129 may have a first recess 124 separated by the first longitudinal channel 122, and each of the third and fourth longitudinal walls 138, 139 may have a second recess 134 separated by the second longitudinal channel 132.

The recesses 124, 134 may secure the surgical clip 200 to the clip applier 10 during loading by releasably receiving or holding the boss members 212, 214 of the first and second leg members 202, 204. The recesses 124, 134 may have a cross-section that corresponds to the boss members 212, 214. Thus, as illustrated, the recesses 124, 134 may be substantially semi-circular grooves to receive a circular cross-section of the boss members 212, 214. However, the recesses 124, 134 may have other shapes for other shapes of the boss members 212, 214. During application, the clip applier 10 may press the first and second leg members 202, 204 against each other through the engagement with the boss members 212, 214 to close the surgical clip 200, as further discussed herein. The first longitudinal channel 122 may receive at least a portion of the first leg member 202 during loading and/or application, and/or the second longitudinal channel 132 may receive at least a portion of the second leg member during loading and/or application.

The first and second stabilizing members 126, 136 may be configured to apply lateral forces to the proximal portion of the surgical clip 200 (e.g., the hinge member 206) to laterally stabilize the surgical clip 200 and/or prevent or reduce fish-tailing. The stabilizing members 126, 136 may be integral to the respective jaw member 102, 104. The stabilizing members 126, 136 may be substantially rigid and extend substantially parallel to a longitudinal axis of the jaw members 102, 104 in the open and closed configurations, and create a longitudinal space therebetween that receives the surgical clip 200, thus the stabilizing members 126, 136 may be positioned on opposite sides of a proximal portion of the surgical clip 200. The stabilizing members 126, 136 may not proximally abut the surgical clip 200 to allow the leg members 202, 204 to elongate as the hook portion 208 deflects around the tip member 210 during closure. The stabilizing members 126, 136 may be received in a widened proximal portion 123, 133 of the longitudinal channel 122, 132 of the opposing jaw member 102, 104 when the clip applier 10 is in the closed configuration. Further features and embodiments of the stabilizing members 126, 136 are further disclosed in U.S. Patent Publication No 2021/0007751, the entire disclosure of which is expressly incorporated herein by reference.

At least one of the first and second jaw members 102, 104 (e.g., both) may have a slanted or angled distal surface 110 on the distal portions 106 to assist with initial trocar entry and navigation of the jaw mechanism 16 intracorporeally. The angled surfaces 110 may further assist in loading of the surgical clip 200, by providing a camming surface to guide the surgical clip 200 to a position between the first and second jaw members 102, 104. The angled surfaces 110 may be symmetric about a central plane of the clip applier 10. The angled distal surfaces 110 may extend substantially the entire height of each the first and second jaw members 102, 104 in the vertical or compression direction to form an outer distal tip 112 on the first and second jaw members 102, 104.

As further illustrated in FIG. 4, at least one of the distal portions 106 of the first and second jaw members 102 may be asymmetric about a medial plane (MP) of the clip applier 10. For example, the distal portion 106 of the first jaw member 102 may have a first width (W1) between a first side surface of the first jaw member 102 and the medial plane (MP) and a second width (W2) between a second side surface of the first jaw member 102 and the medial plane (MP). Similarly, the distal portion 106 of the second jaw member 104 may have a third width (W3) between a first side surface of the second jaw member 104 and the medial plane (MP) and a fourth width (W4) between a second side surface of the second jaw member 104 and the medial plane (MP). As illustrated, the first width (W1) and the fourth width (W4) may be vertically aligned, and the second width (W2) and the third width (W3) may be vertically aligned. The first width (W1) and the third width (W3) may be on opposite sides of the medial plane (MP), and the second width (W2) and the fourth width (W4) may be on opposite sides of the medial plane (MP). The first width (W1) may be greater than the second width (W2), and/or the third width (W3) may be greater than the fourth width (W4). In some embodiments, the first width (W1) and the third width (W3) may be equal, and the second width (W2) and the fourth width (W4) may be equal to make the first and second jaw members 102, 104 radially symmetric about a central point when assembled. Thus, when radially symmetric, the first and second jaw members 102, 104 may be inserted into the cartridge 300 in either 180 degree orientation. The radial symmetry may also facilitate the manufacture of the clip applier 10, producing the first and second jaw members 102, 104 to be at least substantially identical (one being rotated to assemble) and manufactured in the same process (e.g., with the same mold). However, in some embodiments (not shown), the first and second jaw members 102, 104 may not be identical. For example, the first and second jaw members 102, 104 may be radially asymmetric when assembled, such that the first width (W1) and the third width (W3) may not be equal, and/or the second width (W2) and the fourth width (W4) may not be equal. When radially asymmetric, the jaw members 102, 104 may be keyed to the cartridge 300 in a way that only allows insertion of the jaw members 102, 104 in a single orientation. For example, the clip applier 10 may be sized such that the first jaw member 102 can only be inserted into a portion of the cartridge 300 housing the first leg member 202, and the second jaw member 104 can only be inserted into a portion of the cartridge 300 housing the second leg member 204. The radial asymmetry may be applicable, for example, in embodiments where the first leg member 202 and the second leg member 204 have substantially different lengths and/or require different jaw structures for engagement.

The asymmetry of the first jaw member 102 and/or second jaw member 104 about the medial plane (MP) may be at least partially defined by different widths of distal portions of the first and second longitudinal walls 128, 129, and/or different widths of distal portions of the third and fourth longitudinal walls 138, 139. As illustrated, the first longitudinal wall 128 and the fourth longitudinal wall 139 may be vertically aligned, and the second longitudinal wall 129 and the third longitudinal wall 128 may be vertically aligned. The first longitudinal wall 128 and the third longitudinal wall 138 may be on opposite sides of the medial plane (MP), and the second longitudinal wall 129 and the fourth longitudinal wall 139 may be on opposite sides of the medial plane (MP). The distal portion of the first longitudinal wall 128 may have a width greater than a width of the distal portion of the second longitudinal wall 129, and/or the distal portion of the third longitudinal wall 138 may be greater than the distal portion of the fourth longitudinal wall 139. Furthermore, the first jaw member 102 may be asymmetric about the medial plane (MP) along a transverse plane of the at least one recess 124, and/or the second jaw member 104 may be asymmetric about the medial plane (MP) along a transverse plane of the at least one recess 134. Due to the greater widths, the first and third longitudinal walls 128, 138 may include a side wall or end cap 140 on side surfaces of the clip applier 10 that closes the peripheral side of the respective recess 124, 134, improving retention of the boss member 212, 214 received therein and longitudinal alignment of the surgical clip. Due to the reduced widths, the second and fourth longitudinal walls 129, 139 may include open lateral surfaces of the respective recess 124, 134 on side surfaces of the clip applier 10, allowing visualization of the boss member 212, 214 received therein to ensure proper retention.

Figure 5:
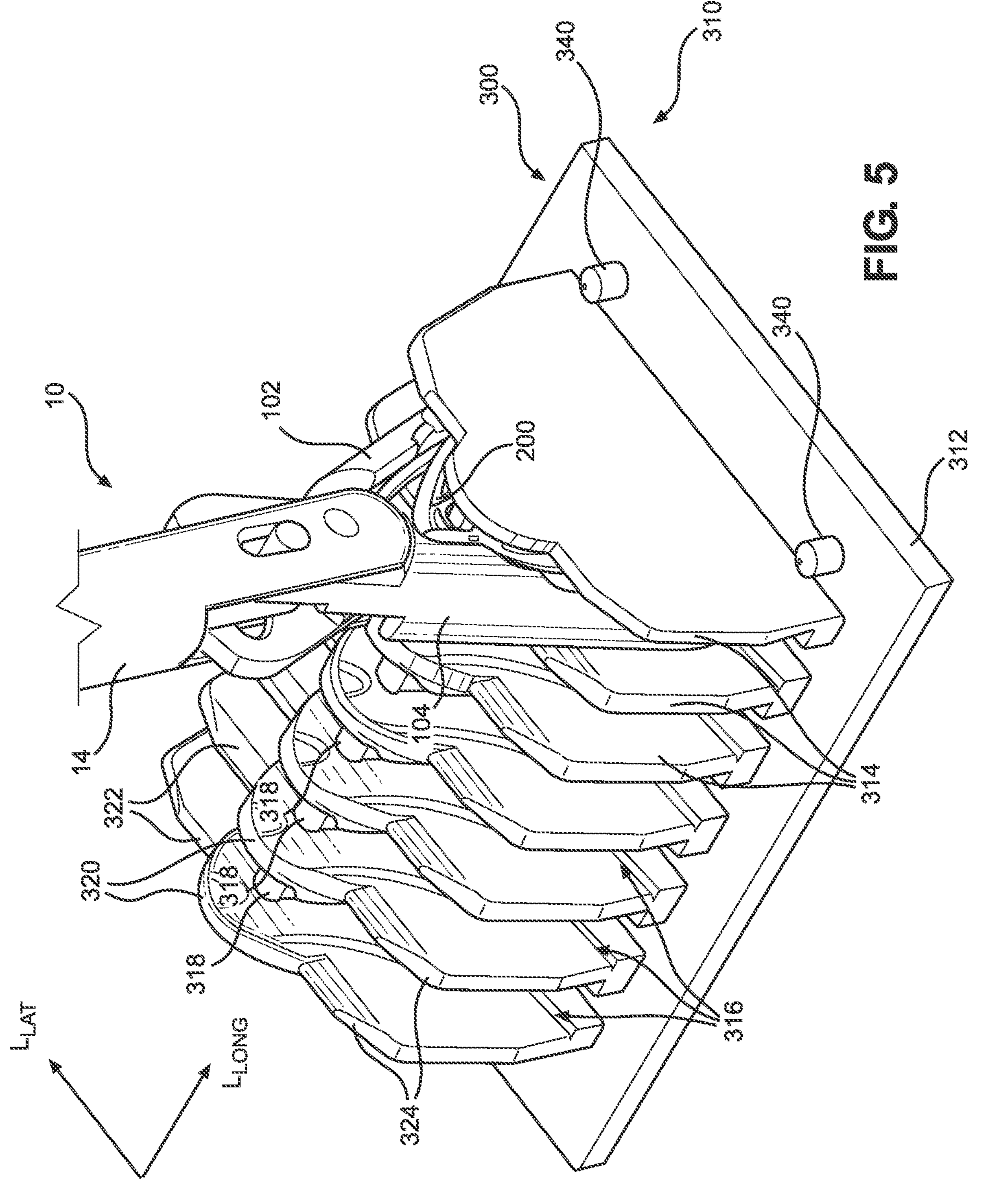
FIG. 5 illustrates a perspective view of the clip applier of FIG. 1 being loaded with the surgical clip from a clip cartridge according to the present invention.
Figure 6:
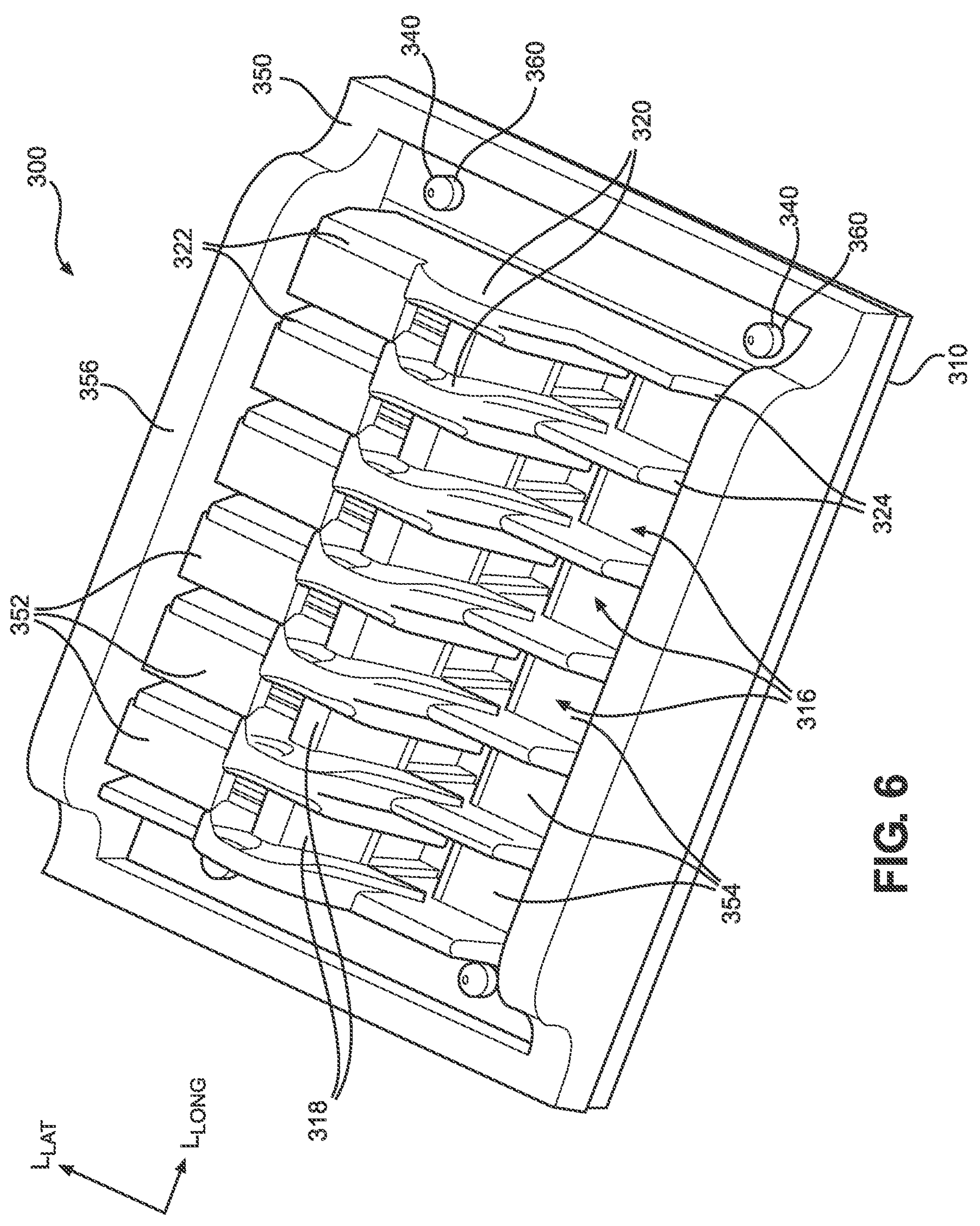
FIG. 6 illustrates a perspective view of the clip cartridge of FIGS. 4 and 5.
Figure 7:
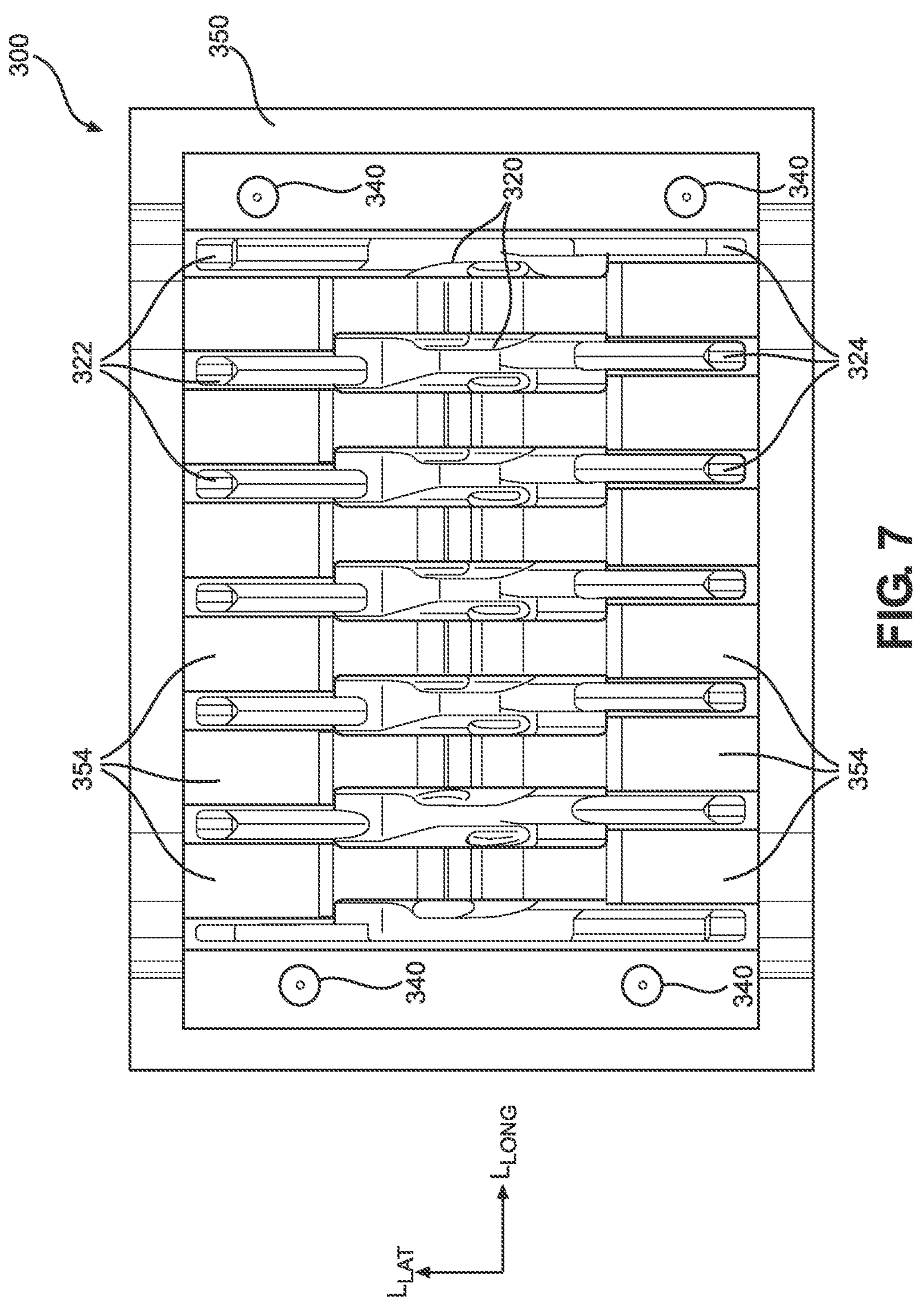
FIG. 7 illustrates a top view of the clip cartridge of FIGS. 4-6.

FIGS. 5-7 illustrate a cartridge 300 configured to be loaded with the surgical clip 200. The cartridge 300 may include a cartridge body 310 and a flexible retainer 350 (as illustrated in FIGS. 6 and 7).

The cartridge body 310 may include abase 312 and a plurality of walls 314 extending from the base 312, where adjacent walls 314 may define one or more cavities 316 therebetween. One or more surgical clip(s) 200 may be supported by one or more support members 318 positioned in the cavities 316 extending between adjacent walls 314. For example, the hinge member 206 of each surgical clip 200 may engage the support member 318, and the first and second leg members 202, 204 may straddle opposing sides of the support member 318. The support members 318 may extend between central portions 320 of adjacent walls 314 along a longitudinal axis ($L_{LONG}$) of the cartridge body 310 or base 312 FIG. 5 illustrates the clip applier 10 being loaded with the surgical clip 200 from the cartridge 300. The cartridge 300 may receive the surgical clip 200 in the cavity 316 in a stored configuration. The cartridge 300 may receive the clip applier 10 in an open configuration to load the surgical clip 200 onto the clip applier 10.

At least one of the walls 314 may include a first wall portion 322 and a second wall portion 324 extending from the central portions 320 perpendicular to the longitudinal axis and along a lateral axis ($L_{LAT}$). The first wall portions 322 may be parallel to each other in the lateral direction and coterminous with each other along a longitudinal line on each end. Similarly, the second wall portions 324 may be parallel to each other in the lateral direction and coterminous with each other along a longitudinal line on each end. Adjacent first wall portions 322 may define a portion of the cavity 316 that receives the first leg member 202, and adjacent second wall portions 324 may define a portion of the cavity 316 that receives the second leg member 204. For at least one of the walls 314, the first wall portion 322 and the second wall portion 324 may be staggered and/or offset relative to each other and/or the central portion 320 with respect to the lateral axis. For example, in some embodiments, a lateral axis extending through the center of the first wall portion 322 may not align with a lateral axis extending through the center of the second wall portion 324. Furthermore, a lateral axis extending through the center of the central portion 320 may not align with at least one of the lateral axes extending through the center of first and second wall portions 322, 324. In some embodiments, the entire width (in the longitudinal direction) of the first wall portion 322 may not overlap with the entire width (in the longitudinal direction) of the second wall portion 324 with respect to a lateral axis. Furthermore, the width (in the longitudinal direction) of each of the first and second wall portions 322, 324 may be less than a width (in the longitudinal direction) of the central portion 320. Thus, in some embodiments, all of the first wall portions 322 and all of the second wall portions 324 may extend offset from each other with respect to a lateral axis of the cartridge body 310. Therefore, the cartridge body 310 and/or the one or more cavities 316 may be asymmetric about a medial plane along the lateral axis of the cartridge body 310 to facilitate keying with the clip applier 10. The cartridge body 310 and/or the one or more cavities 316 may be radially symmetric about a central point to facilitate manufacturing. For example, the cartridge body 310 and/or the one or more cavities 316 may have radial symmetry about a respective center point. However, in some embodiments (not shown), one or more of the cavities 316 may be radially asymmetric, such that the jaw members 102, 104 may be keyed to the cartridge 300 in a way that only allows insertion of the jaw members 102, 104 in a single orientation, as discussed above. For example, the clip applier 10 may be sized such that the first jaw member 102 is intended to engage only the first leg member 202, and the second jaw member 104 is intended to engage only the second leg member 204.

The flexible retainer 350 may be positioned over the cartridge body 310 to cover the base 312. The flexible retainer 350 may be formed separately and secured to the base 312 with apertures 360 of the flexible retainer 350 that receive pins 340 extending from the base 312. The flexible retainer 350 may include a plurality of tabs 352, 354 extending laterally inward from a perimeter 356 of the flexible retainer 350 into the cavities 316 to secure the surgical clip 200 in the cartridge 300. The tabs 352, 354 may engage the leg members 202, 204 and/or boss members 212, 214 to prevent the surgical clip 200 from falling out of the cartridge 300 during storage and/or shipping. The tabs 352, 354 may deflect downward as the first and second jaw members 102, 104 are inserted into the cavities 316 to release the surgical clip 200 from the flexible retainer 350. The plurality of tabs 352, 354 may include first tabs 352 extending between adjacent first wall portions 322 on a first side of the longitudinal axis of the cartridge 300 and second tabs 354 extending between adjacent second wall portions 324 on a second side of the longitudinal axis of the cartridge 300. As further illustrated in FIG. 7, a lateral axis of the first tabs and a lateral axis of the second tabs may be offset to match and interleave with the offset configuration of the first and second wall portions 322, 324, as discussed above. The perimeter 356 may be formed by one or more vertical walls extending around the flexible retainer 350 to increase the security of attachment between the flexible retainer 350 and the cartridge body 310.

The cartridge body 310 may be integrally formed. For example, the components may be a unitary plastic body and formed through injection molding. However, it is contemplated that one or more of the components may be formed separately and attached, for example, through welding or an adhesive. Further discussion of the retention of the surgical clip 200 and/or manufacturing of the cartridge 300 can be found in U.S. Pat. No. 6,880,699, the entire disclosure of which is expressly incorporated herein by reference.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A clip applier configured to apply a surgical clip, the clip applier comprising:

a first jaw member configured to engage a first leg member of the surgical clip, the first jaw member including a first longitudinal wall and a second longitudinal wall;

a second jaw member configured to engage a second leg member of the surgical clip, the second jaw member including a third longitudinal wall and a fourth longitudinal wall;

a first longitudinal channel separating the first and second longitudinal walls of the first jaw member; and a second longitudinal channel separating the third and fourth longitudinal walls of the second jaw member;

wherein at least one of the first jaw member and the second jaw member is asymmetric about a medial plane of the clip applier, and wherein a distal portion of the first longitudinal wall has a first width, a distal portion of the second longitudinal wall has a second width, a distal portion of the third longitudinal wall has a third width, a distal portion of the fourth longitudinal wall has fourth width, and the first width is greater than the second width and/or the third width is greater than the fourth width.

2. The clip applier of claim 1, wherein both of the first jaw member and the second jaw member are asymmetric about the medial plane of the clip applier.

3. The clip applier of claim 1, wherein at least one of the first and second jaw members has a first width on a first side of the medial plane of the clip applier and a second width on a second side of the medial plane of the clip applier, and the first width is greater than the second width.

4. The clip applier of at claim 1, wherein the first jaw member includes a first longitudinal channel extending through a distal end of the first jaw member, and/or the second jaw member includes a second longitudinal channel extending through a distal end of the second jaw member.

5. The clip applier of claim 1, wherein the first jaw member includes at least one first recess configured to receive at least one boss on the first leg member, the second jaw member includes at least one second recess configured to receive at least one boss on the second leg member, and at least one of the first jaw member and the second jaw member are asymmetric about the medial plane of the clip applier along the at least one first recess and the at least one second recess.

6. The clip applier of claim 5, wherein the first jaw member has a closed lateral side of the at least one first recess, and the second jaw member has a closed lateral side of the at least one second recess.

7. The clip applier of claim 5, wherein the at least one first recess of the first jaw member has an open lateral side and a closed lateral side, and the at least one second recess of the second jaw member has an open lateral side and a closed lateral side.

8. The clip applier of claim 1, wherein at least one of the first and second jaw members includes a stabilizing member configured to laterally stabilize a proximal portion of the surgical clip when the surgical clip is in an open configuration.

9. The clip applier of claim 8, further comprising a longitudinal channel in at least one of the first and second jaw members configured to receive the stabilizing member of the at least one of the first and second jaw members when the clip applier is in a closed configuration.

10. The clip applier of claim 8, wherein the first jaw member includes a first stabilizing member, the second jaw member includes a second stabilizing member, and the first stabilizing member and the second stabilizing member are configured to receive the proximal portion of the surgical clip when the surgical clip is in an open configuration.

11. A clip applier system comprising:

the clip applier of claim 1; and a clip cartridge having at least one cavity configured to receive the clip applier to load the surgical clip, wherein the at least one cavity is asymmetric about a medial plane.

12. The clip applier system of claim 11, wherein the at least one cavity is formed by offset wall portions of the clip cartridge.

* * * * *